(12) United States Patent
Fox et al.

(10) Patent No.: US 11,680,927 B1
(45) Date of Patent: Jun. 20, 2023

(54) DUAL LAYER CIRCUIT BOARD FOR SENSORS ON A PIPELINE INSPECTION TOOL

(71) Applicants: Arthur Fox, Murray, UT (US); Calvin L. Simmons, Murray, UT (US); Michael P. Sheffield, Lake Point, UT (US); William Geoffrey Callahan, Cedar Hills, UT (US)

(72) Inventors: Arthur Fox, Murray, UT (US); Calvin L. Simmons, Murray, UT (US); Michael P. Sheffield, Lake Point, UT (US); William Geoffrey Callahan, Cedar Hills, UT (US)

(73) Assignee: Cypress In-Line Inspection, LLC, Tulsa, OK (US)

( * ) Notice: Subject to any disclaimer, the term of this patent is extended or adjusted under 35 U.S.C. 154(b) by 2 days.

(21) Appl. No.: 17/199,694

(22) Filed: Mar. 12, 2021

Related U.S. Application Data

(63) Continuation-in-part of application No. 16/953,626, filed on Nov. 20, 2020, now abandoned.

(60) Provisional application No. 62/939,059, filed on Nov. 22, 2019.

(51) Int. Cl.
  *G01N 27/82*   (2006.01)
  *G01N 33/2045* (2019.01)

(52) U.S. Cl.
  CPC ......... *G01N 27/82* (2013.01); *G01N 33/2045* (2019.01)

(58) Field of Classification Search
  CPC .......................... G01N 27/82; G01N 33/2045
  See application file for complete search history.

(56) References Cited

U.S. PATENT DOCUMENTS

| | | | |
|---|---|---|---|
| 3,832,603 A | 8/1974 | Cray et al. | |
| 5,111,200 A | 5/1992 | Jasmer et al. | |
| 5,745,258 A | 4/1998 | Kawabata et al. | |
| 5,986,887 A | 11/1999 | Smith et al. | |
| 6,351,116 B1* | 2/2002 | Bolda | G01R 35/005 |
| | | | 324/202 |
| 6,686,222 B2 | 2/2004 | Omizo et al. | |
| 6,847,207 B1* | 1/2005 | Veach | G01N 27/902 |
| | | | 324/220 |
| 10,455,738 B2 | 10/2019 | Pakula et al. | |
| 2007/0022830 A1* | 2/2007 | Mandziuk | G01N 27/902 |
| | | | 73/865.8 |
| 2007/0028706 A1* | 2/2007 | Mandziuk | F16L 55/38 |
| | | | 73/865.9 |

(Continued)

*Primary Examiner* — Dominic E Hawkins
(74) *Attorney, Agent, or Firm* — Chad Hinrichs, PLLC

(57) ABSTRACT

The present invention provides a way to increase the density of Hall effect sensors on a MFL inline inspection tool mounting the sensors on a first circuit board which overlies a second circuit board. Op amps for the sensors which condition and filter the analog signal from the sensors are mounted on the first circuit board. Microprocessors mounted on the second circuit board receive the analog signal from the op amp and translate it into a digital signal. Use of the stacked circuit boards doubles the amount of area to mount the sensors and their op amps and microprocessors while maintaining the same footprint. This results in being able to increase the number of Hall effect sensors in that footprint area. In other embodiments the number of layers of circuit boards may be increased beyond two.

12 Claims, 5 Drawing Sheets

(56) References Cited

U.S. PATENT DOCUMENTS

| | | | | |
|---|---|---|---|---|
| 2008/0042646 | A1* | 2/2008 | Burkhardt | G01N 27/82 324/240 |
| 2012/0109565 | A1* | 5/2012 | Tsukada | G01N 27/83 702/106 |
| 2018/0045680 | A1* | 2/2018 | Thompson | G01R 33/072 |

* cited by examiner

DUAL LAYER CIRCUIT BOARD FOR SENSORS ON A PIPELINE INSPECTION TOOL

PRIORITY CLAIM

The present application claims priority to and is a continuation-in-part application of U.S. non-provisional patent application Ser. No. 16/953,626 filed on Nov. 20, 2020 entitled Improved Magnetic Flux Leak Inline Inspection Tool which claims priority to and is a continuation-in-part of U.S. provisional patent application number 62/939,059 filed on Nov. 22, 2019 entitled Improved Magnetic Flux Leak Inline Inspection Tool, both of which are incorporated herein by reference.

FIELD OF THE INVENTION

The present invention relates generally to a magnetic flux leakage (MFL) inline inspection tool for pipelines and other conduits. More particularly, the present invention relates to the use of two layers of circuit boards used to increase the density of Hall effect sensors and provide a more detailed inspection of the pipe wall.

BACKGROUND OF THE INVENTION

Performance of a MFL inline pipeline inspection tool is dependent upon the number of Hall effect sensors used. The greater the number of sensors used the better the resolution of the search. With higher resolution the tool is capable of locating smaller defects.

In a typical MFL inline inspection tool a plurality of Hall effect sensors and their op amps, and microprocessors are mounted on a single printed circuit board. Each sensor typically has its own op amp. The sensor sends an analog signal to its op amp which conditions and filters the signal. A microprocessor receives the analog signals from the op amps of several sensors. With the current technology, a microprocessor typically processes the signals of eight sensors.

One of the limiting factors in the number of sensors and in turn the density of sensors (number of sensors per unit of area) is the size limitations of the printed circuit board. Simply put, more sensors could be added but there is not enough room on the circuit board for additional sensors, their op amps and microprocessors. What is needed, is a way to increase the density of the Hall effect sensors on these inline inspection tools.

BRIEF SUMMARY OF THE INVENTION

The present invention provides a way to increase the density of Hall effect sensors on a MFL inline inspection tool. In the preferred embodiment there is a first circuit board which overlies a second circuit board. This doubles the amount of area to mount the sensors and their op amps and microprocessors while maintaining the same footprint. This results in being able to double the number of Hall effect sensors in that footprint area. In other embodiments the number of layers of circuit boards may be increased beyond two.

BRIEF DESCRIPTION OF THE DRAWINGS

Preferred embodiments of the invention will now be described in further detail. Other features, aspects, and advantages of the present invention will become better understood with regard to the following detailed description, appended claims, and accompanying drawings (which are not to scale) where:

DETAILED DESCRIPTION OF THE PREFERRED EMBODIMENT(S)

Figure 1:
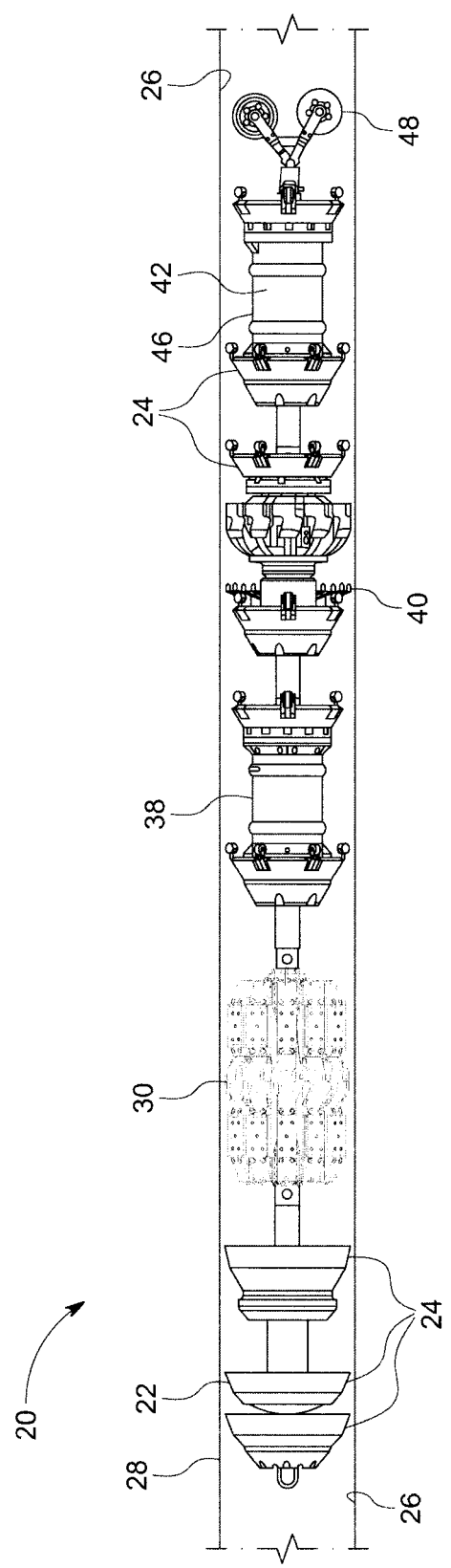
FIG. 1 is a diagram of a typical inline inspection tool of the present invention.

The preferred embodiment of the present invention is used with a MFL inline inspection tool 20 typically having several sections, as best seen in FIG. 1. The first section is the tow 22. It has a plurality urethan vanes, commonly called cups 24. The cups 24 extend radially outward from the outer circumference of the tow 22 and create a loose seal between the tow 22 and the interior wall 26 of the pipe 28. This seal allows the fluid in the pipe 28 to move the tool 20 along the pipe 28 as the fluid is conveyed through pumping or compression action. It should be noted the fluid in the pipe 28 could be a gas or a liquid. Other sections of the tool 20 may also be equipped with cups 24.

The second section of the tool 20 is the magnetizer 30 this is the section of the tool 20 which carries the magnets 50. The magnets 50 create the magnetic field in the pipe 28. The Hall effect sensors 34 measure the magnetic field in the pipe 28 and search for magnetic field leakage caused by defects attributable to metal loss in the pipe 28. The magnetizer 30 has a plurality of sensor arms 36 which extend radially outward. Each arm 36 carries an array of sensor 34. The arrays of sensors 34 are discussed in greater detail below.

The third section of the tool 20 is the data collection and battery section 38. Data from the sensor 34 on the magnetizer 30 and the geometry sensor 40 are further processed and stored here. The batteries 42 provide power to operate the sensors 34 and data storage.

The fourth section of the tool 20 is the geometry sensor 40. It has a plurality of arms 40 which extend from the body 44 of the tool 20 and determine the interior diameter of the pipe 28. This is used to locate dents in the pipe 28 and sections which are out of round.

The fifth section of the tool 20 is the inertial mapping unit or IMU 46. It has micro processing capability and batteries which provide power for the operation of the tool 20. The primary purpose of the IMU 46 is to calculate data and correlate the location of the tool 20 in the pipeline 28 with the location of defects.

The sixth section of the tool 20 is the odometer 48. It measures the distance the tool 20 has traveled and provides related data to the IMU 46.

It should be noted the order of the sections of the tool 20 are mentioned above for ease of description and explanation. The exact order of the sections may vary. Further it may be possible to have a tool 20 without one of the fore mention sections and still fall within the scope of protection of this patent.

Figure 2:
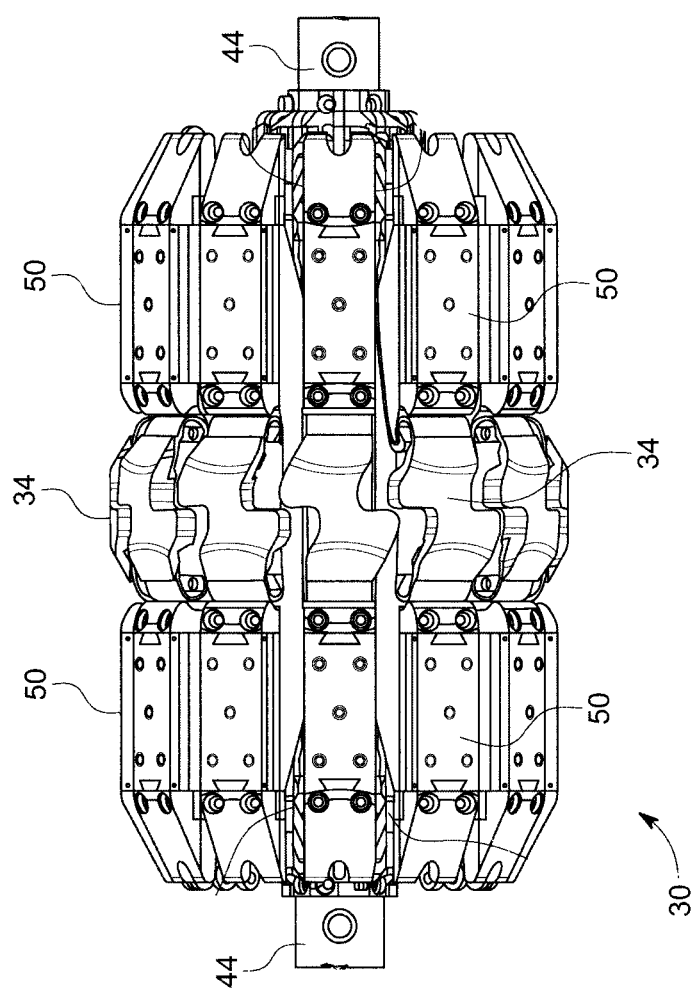
FIG. 2 is side view of the preferred embodiment of magnetizer of the present invention.
Figure 3:
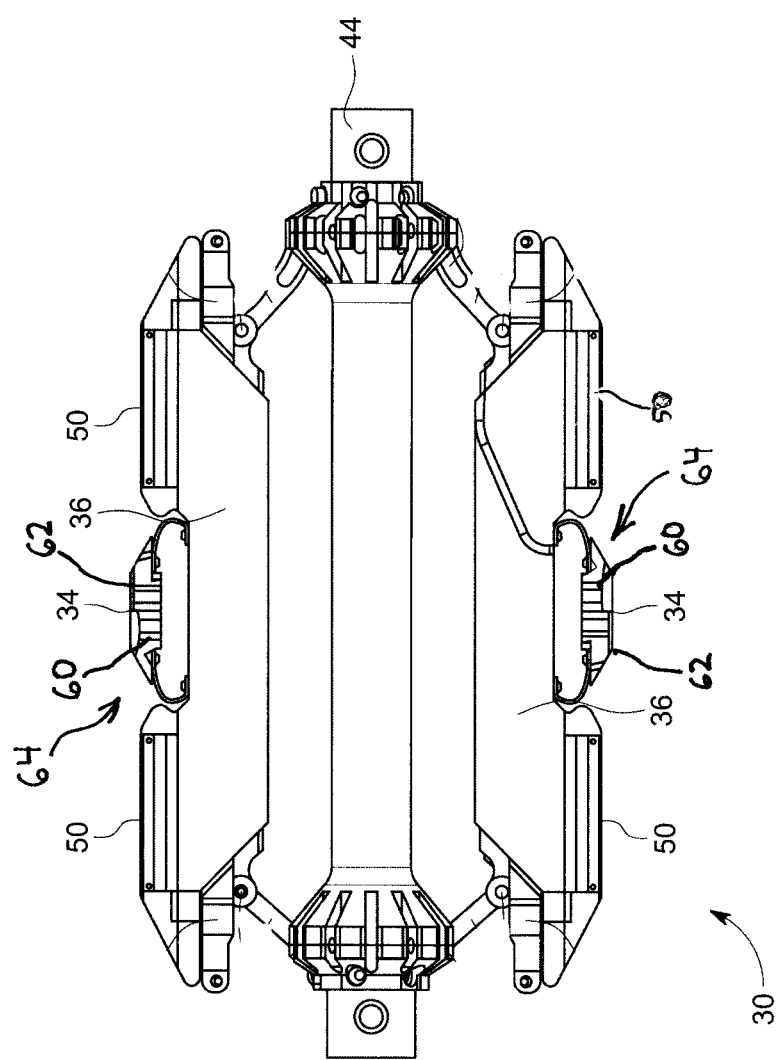
FIG. 3 is a sectional view of the preferred embodiment of the magnetizer of the present invention showing two of the sensor arms.

The magnetizers 30 of an MFL inline pipeline inspection tools 20 typically have a plurality of Hall effect sensors 34 and magnets 50 which are located around the body of the tool 20. In the preferred embodiment of the present invention the sensors 34 and magnets 50 ride on a plurality of arms 36 which extend radially outward from the tool 20. See FIGS. 2-4. This is to ensure the arms 36 and their sensors 34 and magnets 50 are adjacent to the wall of the pipe 28 being inspected.

Each arm 36 has a pair of magnets 50, one located on each end of the arm 36 with the sensors 34 located between the magnets 50. The pair of magnets 50 on each are comprised of a north polarity magnet and a south polarity magnet 50. Movement of the arms 36 maintains the sensors 34 and magnets 50 in close proximity to the interior wall 26 of the pipe 28 as the tool 20 moves through the pipe 28 or other conduit being inspected.

Figure 4:
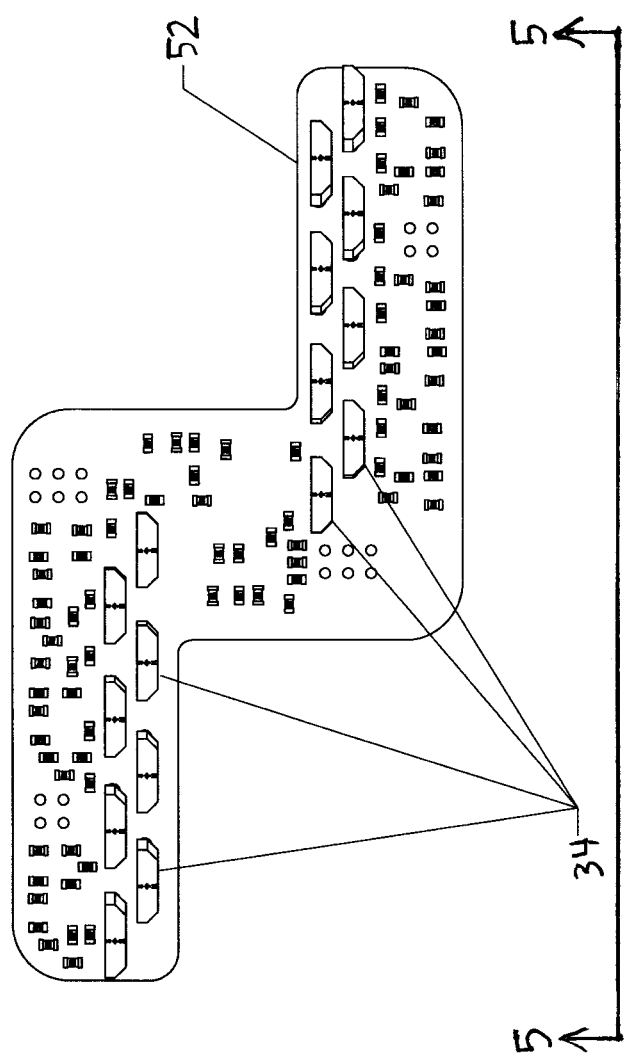
FIG. 4 is a top view of the preferred embodiment of a Hall effect sensor array with dual circuit boards.
Figure 5:
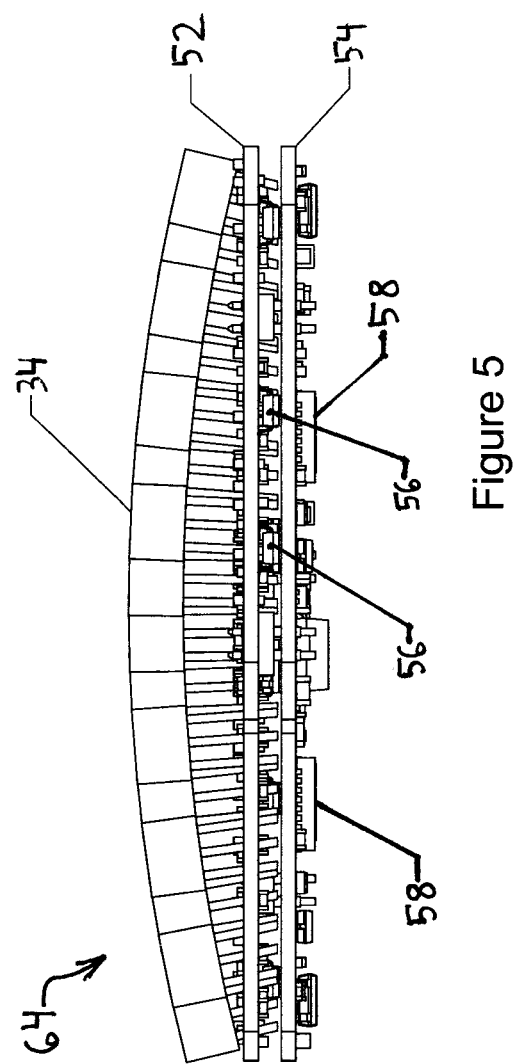
FIG. 5 is a side view of the preferred embodiment of a Hall effect sensor array with a dual circuit boards.

As best seen in FIGS. 4 and 5, the Hall effect sensor arrays 64 are comprised of a plurality of Hall effect sensors 34, op amps 56 and microprocessors mounted on two or more circuit boards 52 and 54. The preferred embodiment of the present invention uses a double layer of circuit boards 52 and 54. See FIGS. 4-5. A first circuit board 52 with a footprint overlies the footprint of a second circuit board 54.

While the drawings show a first circuit boards 52 and 54, one on top of the other, the present invention could be practiced with more than two circuit boards 52 and 54 stacked on top of one another.

The magnets 50 located on either side of the Hall effect sensors 34 create a magnetic field in the pipe 28 and adjacent to the interior wall 26. The Hall effect sensors 34 detect and generate an analog signal based upon this magnetic field. The magnetic field remains constant so long as there are no changes in pipe 28. However, if there are defects caused by metal loss such as corrosion or pitting, there will be variations in the magnetic field. These variations in the magnetic field result in variations in the signal from the Hall effect sensors 34.

Performance of the tool 20 is dependent upon the number of Hall effect sensors 34 used. The greater the number of sensors 34 used the better the resolution of the search and the smaller the defects that can be located. The present invention increases the density of the sensors 34 by stacking printed circuit boards 52 and 54 on top of one another. This creates enough surface area on the circuit boards 52 and 54 to mount the Hall effect sensors 34 and their supporting op amps 56 and microprocessors 58.

Each of the Hall effect sensors 34 are electrically connected to their own op amp 56. The op amp 56 receives the analog signal from their respective Hall effect sensor 34. The op amps 56 condition and filter the signals from the Hall effect sensors 34. Each op amp 56 is electronically connected to a microprocessor 58. The signal from the op amp 56 is sent to a microprocessor 58 where it is converted into a digital signal. Based on current technology, one microprocessor 58 can process the signals from up to eight Hall effect sensors 34 . However, as the technology of microprocessors 58 advances, in the future they could be capable of processing the signals originating from more than eight Hall effect sensors 34.

In the preferred embodiment, the Hall effect sensors 34 and their op amps 56 are mounted on one of the circuit boards 52 or 54 and the microprocessors 58 are mounted on the other circuit boards 52 or 54. Thus the analog and digital signals are segregated from one another. All of the analog signals are mostly limited to one of the circuit boards 52 or 54 and the digital signals are limited to the other circuit board 52 or 54. In the preferred embodiment shown, the Hall effect sensors 34 and op amps 56 are mounted on the first (top) circuit board 52 and the microprocessors 58 are mounted on the second (bottom) circuit board 54. In this case the analog signals are primarily limited to the first (top) circuit board 52 and the digital signals are limited to the second (bottom) circuit board 54.

As can be seen in the drawings the leads from the sensors 34 are mounted on the first (top) circuit board 52 and extend away from the first circuit board 52 and to the sensor 34 itself. The sensors 34 are embedded in a protective block 60. In the preferred embodiment the block 60 is a nonconductive resin. The block 60 of resin and sensors 34 may be contained inside a metallic wear shield 62. This arrangement protects the sensors 34 from abrasion against the interior wall of the pipe as the tool travels through the pipe and related vibration.

Other embodiments may include half the sensors 34 and their op amps 56 and microprocessors 58 mounted on the first (top) circuit board 52 and half of the sensors 34 pass through the first (top) circuit board 52 and are mounted to the second (bottom) circuit board 54. In this embodiment the op amps 56 and microprocessors 58 are mounted on the same circuit board 52 or 54 as their respective sensor 34. This provides the sufficient board space to mount the additional sensors 34.

Further embodiments may include eliminating the use of op amps 56. In this embodiment the signals from the Hall effect sensors 34 go directly to a microprocessor 58.

The foregoing description details certain preferred embodiments of the present invention and describes the best mode contemplated. It will be appreciated, however, that changes may be made in the details of construction and the configuration of components without departing from the spirit and scope of the disclosure. Therefore, the description provided herein is to be considered exemplary, rather than limiting, and the true scope of the invention is that defined by the following claims and the full range of equivalency to which each element thereof is entitled.

What is claimed is:

1. An array of Hall effect sensors for a pipeline inline inspection tool comprising:
    a first circuit board with a footprint overlying a footprint of a second circuit board;
    a plurality of Hall effect sensors mounted on the first circuit board; and
    one or more microprocessors mounted on the second circuit board;
    wherein, the Hall effect sensors generate an analog signal and the microprocessor receives the analog signal and translates it to a digital signal.

2. The array of Hall effect sensors of claim 1 further comprising:
    a plurality of op amps mounted on the first circuit board, each op amp electrically connected to one of the Hall effect sensors;
    wherein the Hall effect sensor sends the signal to its op amp and the op amp filters the signal.

3. The array of Hall effect sensor of claim 2, further comprising:
    an electrical connection between each op amp and one of the microprocessors;
    wherein, the microprocessor receives the signal from the op amp and translates it to a digital signal.

4. The array of Hall effect sensors of claim 3, further comprising:
    all processing of analog signals occurs on the first circuit board.

5. The array of Hall effect sensors of claim 3, further comprising:
    all processing of digital signals occurs on the second circuit board.

6. The array of Hall effect sensors of claim 3, further comprising:
    the Hall effect sensors extending above the first circuit board; and
    a block encasing the Hall effect sensors.

7. The array of Hall effect sensors of claim 6, the block comprising:
    an electrically nonconductive resin.

8. The array of Hall effect sensors of claim 7, further comprising:
    a metallic wear shield;
    wherein the block and sensors are contained within the metallic wear shield.

9. The array of Hall effect sensors of claim 6, further comprising:
    a north pole magnet and a south pole magnet;
    wherein the Hall effect sensors are located between the north pole and south pole magnets.

10. The array of Hall effect sensors of claim 9 further comprising:
    a tool body; and
    a sensor arm;
    wherein the sensor arm extends radially outward form the tool body and the Hall effect sensor array, north pole magnet and south pole magnet are mounted on the sensor arm.

11. An array of Hall effect sensors for a pipeline inline inspection tool comprising:
    a first circuit board with a footprint overlying a footprint of a second circuit board;
    a plurality of Hall effect sensors mounted on the first circuit board, the Hall effect sensors being capable of generating an analog signal;
    a plurality of op amps mounted on the first circuit board, the op amps being capable of receiving the signal from the Hall effect signal and filtering the signal;
    one or more microprocessors mounted on the second circuit board, the microprocessor being capable of receiving the signal from the op amp and translating it to a digital signal;
    a tool body;
    a sensor arm;
    a north pole magnet;
    a south pole magnet;
    a block of electrically nonconductive resin; and
    a metallic wear plate;
    wherein the Hall effect sensors are encased in the block on electrically nonconductive resin covered by the metallic wear plate and are mounted on the sensor arm between the north pole magnet and the south pole magnet;
    wherein the sensor arm moves radially outward from the body; and
    wherein digital signals are only processed on the second circuit board.

12. An array of Hall effect sensors for a pipeline inline inspection tool comprising:
    a first circuit board with a footprint overlying a footprint of a second circuit board;
    a plurality of Hall effect sensors mounted on the first circuit board, the Hall effect sensors being capable of generating an analog signal;
    one or more microprocessors mounted on the second circuit board, the microprocessor being capable of receiving the signal from the Hall effect sensors;
    a tool body;
    a sensor arm;
    a north pole magnet;
    a south pole magnet;
    a block of electrically nonconductive resin; and
    a metallic wear plate;
    wherein the Hall effect sensors are encased in the block of electrically nonconductive resin covered by the metallic wear plate and are mounted on the sensor arm between the north pole magnet and the south pole magnet;
    wherein the sensor arm moves radially outward from the body; and
    wherein all analog signals are processed on the first circuit board and only digital signals are processed on the second circuit board.

\* \* \* \* \*